US007037255B2

(12) United States Patent
Inman et al.

(10) Patent No.: US 7,037,255 B2
(45) Date of Patent: May 2, 2006

(54) SURGICAL INSTRUMENTS FOR ADDRESSING PELVIC DISORDERS

(75) Inventors: Mona J. Inman, Eden Prairie, MN (US); John W. Westrum, Jr., Prior Lake, MN (US); Johannes N. Gaston, Minnetonka, MN (US); Douglas J. VanOmum, Minnetonka, MN (US); Robert E. Lund, St. Michael, MN (US); Brian P. Watschke, Eden Prairie, MN (US); Johann J. Neisz, Coon Rapids, MN (US); Vicki R. Vandersloot, Minneapolis, MN (US)

(73) Assignee: AMS Research Corporation, Minnetonka, MN (US)

( * ) Notice: Subject to any disclaimer, the term of this patent is extended or adjusted under 35 U.S.C. 154(b) by 141 days.

(21) Appl. No.: 10/274,524

(22) Filed: Oct. 17, 2002

(65) Prior Publication Data

US 2003/0065246 A1    Apr. 3, 2003

Related U.S. Application Data

(63) Continuation-in-part of application No. 29/160,922, filed on May 16, 2002, now abandoned, and a continuation-in-part of application No. 10/005,837, filed on Nov. 9, 2001, now abandoned, and a continuation-in-part of application No. 09/917,445, filed on Jul. 27, 2001, now Pat. No. 6,802,807.

(60) Provisional application No. 60/347,494, filed on Jan. 11, 2002, provisional application No. 60/336,884, filed on Nov. 2, 2001, provisional application No. 60/343,658, filed on Oct. 24, 2001.

(51) Int. Cl.
 *A61F 2/02* (2006.01)
(52) U.S. Cl. ...................................................... 600/30

(58) Field of Classification Search ............ 600/29–32; 81/489; 606/185, 190, 222, 223
See application file for complete search history.

(56) References Cited

U.S. PATENT DOCUMENTS

| 2,609,851 | A | * | 9/1952 | Hadfield ..................... 81/489 |
| 3,160,157 | A | * | 12/1964 | Chisman ..................... 606/223 |
| 4,172,458 | A |   | 10/1979 | Pereyra |
| 4,509,516 | A |   | 4/1985 | Richmond |
| 5,019,032 | A |   | 5/1991 | Robertson |
| 5,030,228 | A | * | 7/1991 | Wong et al. ................ 606/223 |
| 5,053,043 | A |   | 10/1991 | Gottesman et al. |

(Continued)

FOREIGN PATENT DOCUMENTS

EP    0470308 A1    2/1992

(Continued)

OTHER PUBLICATIONS

G. Narik et al., A Simplified Sling Operation Suitable for Routine Use, Gynecological and Obstetrical Clinic, University of Vienna, vol. 84, No. 3, p. 400-405, (Aug. 1, 1962).

(Continued)

*Primary Examiner*—Samuel G. Gilbert
(74) *Attorney, Agent, or Firm*—Oblon, Spivak, McClelland, Maier & Neustadt, P.C.

(57) ABSTRACT

A novel surgical instrument is shown and described. The surgical instrument is useful in pelvic floor repair procedures such as sling procedures for treating incontinence. Also, a novel, ornamental design for a handle for a surgical instrument is shown and described.

19 Claims, 10 Drawing Sheets

U.S. PATENT DOCUMENTS

| | | | |
|---|---|---|---|
| 5,109,869 A * | 5/1992 | Buckley | 606/591 |
| 5,112,344 A | 5/1992 | Petros | |
| 5,281,237 A | 1/1994 | Gimpelson | |
| 5,383,901 A * | 1/1995 | McGregor et al. | 606/223 |
| 5,439,467 A * | 8/1995 | Benderev et al. | 606/139 |
| 5,562,689 A | 10/1996 | Green et al. | |
| 5,591,163 A | 1/1997 | Thompson | |
| 5,611,515 A | 3/1997 | Benderev et al. | |
| 5,626,614 A | 5/1997 | Hart | |
| 5,643,292 A * | 7/1997 | Hart | 606/144 |
| 5,681,333 A * | 10/1997 | Burkhart et al. | 606/148 |
| 5,683,415 A | 11/1997 | Brunken | |
| 5,836,314 A | 11/1998 | Benderev et al. | |
| 5,836,315 A | 11/1998 | Benderev et al. | |
| 5,860,425 A | 1/1999 | Benderev et al. | |
| 5,899,909 A | 5/1999 | Claren et al. | |
| 5,904,692 A | 5/1999 | Steckel et al. | |
| 6,030,393 A | 2/2000 | Corlew | |
| 6,168,611 B1 | 1/2001 | Risvi | |
| 6,273,852 B1 | 8/2001 | Lehe et al. | |
| 6,423,080 B1 | 7/2002 | Gellman et al. | |
| 6,447,527 B1 | 9/2002 | Thompson et al. | |
| 6,638,209 B1 * | 10/2003 | Landgrebe | 600/30 |
| 2001/0018549 A1 | 8/2001 | Scetbon | |
| 2001/0023356 A1 | 9/2001 | Raz | |
| 2001/0049467 A1 | 12/2001 | Lehe et al. | |
| 2001/0053916 A1 | 12/2001 | Rioux | |
| 2002/0007222 A1 | 1/2002 | Desai | |
| 2002/0077526 A1 | 6/2002 | Kammerer et al. | |
| 2002/0087183 A1 * | 7/2002 | Boyd et al. | 606/190 |
| 2002/0091298 A1 | 7/2002 | Landgrebe | |
| 2002/0099258 A1 | 7/2002 | Staskin et al. | |
| 2002/0099259 A1 | 7/2002 | Anderson et al. | |
| 2002/0107430 A1 | 8/2002 | Neisz et al. | |
| 2002/0147382 A1 | 10/2002 | Neisz et al. | |
| 2002/0151762 A1 | 10/2002 | Rocheleau et al. | |
| 2002/0151909 A1 | 10/2002 | Gellman et al. | |
| 2002/0151910 A1 | 10/2002 | Gellman et al. | |
| 2002/0156487 A1 | 10/2002 | Gellman et al. | |
| 2002/0156488 A1 | 10/2002 | Gellman et al. | |
| 2002/0156489 A1 | 10/2002 | Gellman et al. | |
| 2002/0173800 A1 | 11/2002 | Dreyfuss et al. | |
| 2003/0009181 A1 | 1/2003 | Gellman et al. | |

FOREIGN PATENT DOCUMENTS

| | | |
|---|---|---|
| EP | 1093758 A1 | 10/2000 |
| WO | WO 98/35616 A1 | 8/1998 |
| WO | WO 00/74594 A1 | 12/2000 |
| WO | WO 02/28312 A1 | 4/2002 |
| WO | WO 02/32284 A2 | 4/2002 |
| WO | WO 02/34124 A2 | 5/2002 |
| WO | WO 02/239890 A2 | 5/2002 |

OTHER PUBLICATIONS

J. Chassar Moir et.al., The Gauze-Hammock Operation, The Journal of Obstetrics and Gynaecology of British Commonwealth, vol. 75 No. 1, pp. 1-9 (Jan. 1968).

Jerry Blaivas et al., Pubovaginal Fascial Sling for the Treatment of Complicated Stress Urinary Incontinence, The Journal of Urology, vol. 145, pp. 1214-1218 (Jun. 1991).

Thomas A. Stamey, M.D., Endoscopic Suspension of the Vesical Neck for Urinary Incotinence in Females, Ann. Surg., vol. 192 No. 4, pp. 465-471 (Oct. 1980).

Peter E. Papa Petros et al., The Autogenic Ligament Procedure: A Technique for Planned Formation of an Artificial Neo-Ligament, Acta Obstet Gynecol Scand, vol. 69, Sup 153, pp. 43-51 (1990).

U. Ulmsten et al., An Ambulatory Surgical Procedure Under Local Anesthesia for Treatment of Female Urinary Incontinence, International Urolgynecology Journal, vol. 7, pp. 81-86, (1996).

Ulf Ulmsten et al., A Three Year Follow Up of Tension Free Vaginal Tape for Surgical Treatment of Female Stress Urinary Incontinence, British Journal of Obstetrics and Gynaecology, vol. 106, pp. 345-350 (1999).

Raymond Rackley, MD., Synthetic Slings: Five Steps for Successful Placement, Urology Times, p. 46,48,49 (Jun. 2000).

Stuart Stanton,Springer-Veglag, Surgery of Female Inc. ontinence, pp. 105-113 (1986).

Raymond R. Rackley, M.D. et al. Tension-free Vaginal Tape and Percutaneous Vaginal Tape Sling Procedures, Techniques in Urology (2001), vol. 7, No. 2, pp. 90-100.

John Klutke, M.D. et al, The promise of tension-free vaginal tape for female SUI, Contemporary Urology, 7 pages (Oct. 2000).

TVT Tension-free Vaginal Tape, Gynecare, Ethicon, Inc., 23 pages (1999).

Donald R. Ostergard et al., Urogynecology and Urodynamics Theory and Practice, pp. 569-579 (1996).

Pat O'Donnell, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).

Jeffrey P. Norris, et al., Use of Synthetic Material in Sling Surgery: A Minimally Invasive Approach, Journal of Endourology, vol. 10, pp. 227-230 (Jun. 1996).

David R. Staskin et al., The Gore-Tex Sling Procedure for Female Sphincteric Incontinence: Indications, Technique, and Results, World Journal of Urology, vol. 15, pp. 295-299 (1997).

Cook/Ob Gyn®, Urogynecology, Copyright Cook Urological Inc., pp. 1-36 (1996).

Shlomo Raz, Female Urology, pp. 80-86, 369-398, 435-442 (1996).

IVS Tunneller, AMA, 3 pages. (EAU 2001).

* cited by examiner

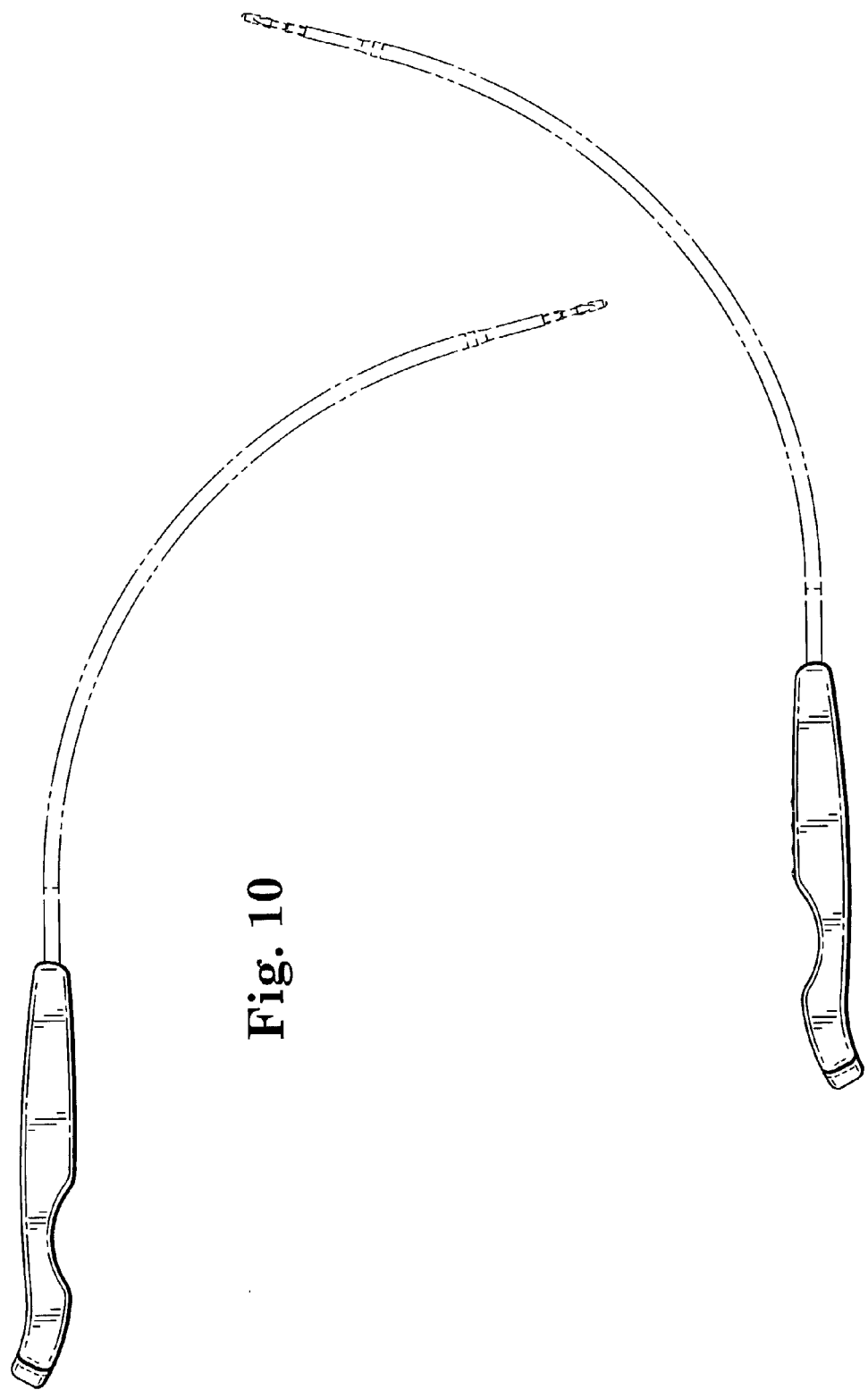

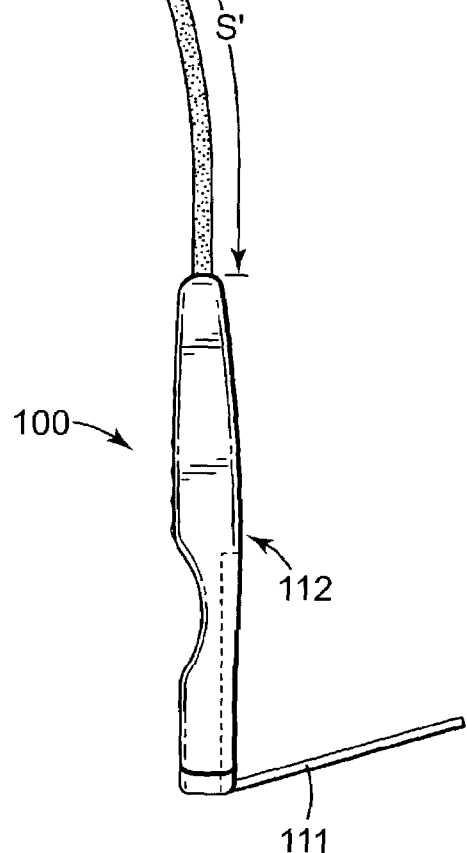
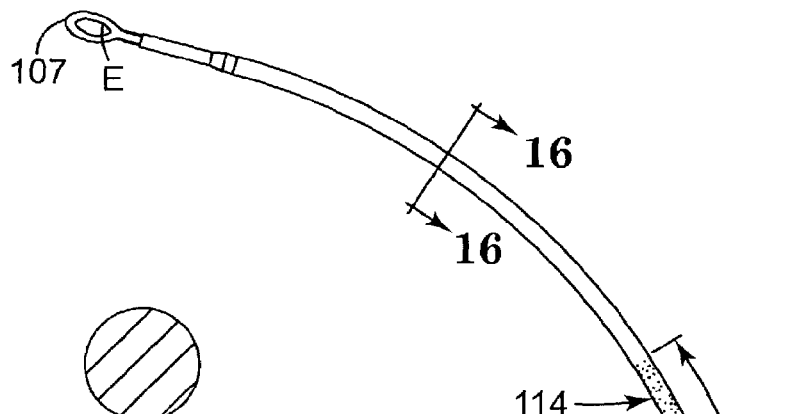
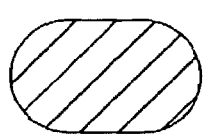
Fig. 16
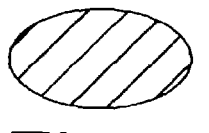
Fig. 17
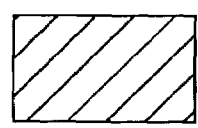
Fig. 18
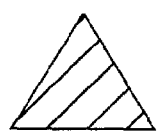
Fig. 19
Fig. 20
Fig. 15

SURGICAL INSTRUMENTS FOR ADDRESSING PELVIC DISORDERS

CROSS REFERENCE TO RELATED APPLICATIONS

The present application is a continuation-in-part of U.S. patent application Ser. No. 09/917,445, filed Jul. 27, 2001, now U.S. Pat. No. 6,802,807; U.S. patent application Ser. No. 10/005,837 now abandoned, filed Nov. 9, 2001 and Design patent application Ser. No. 29/160,922 now abandoned, filed May 16, 2002; and claims priority to U.S. Provisional Application Ser. No. 60/343,658, filed Oct. 24, 2001; and U.S. Provisional Application Ser. No. 60/336,884, filed Nov. 2, 2001; and U.S. Provisional Application Ser. No. 60/347,494, filed Jan. 11, 2002. The entire contents of all of these provisional, utility and design patent applications are herein incorporated by reference.

BACKGROUND

Surgical centers and hospitals have stocks of surgical instruments commonly used in surgery for treating pelvic floor disorders. In the urology field, needles, suture passers and ligature carriers are commonly available. Examples of such surgical instruments include Stamey needles, Raz needles, and Pereyra needles. See Stamey, *Endoscopic Suspension of the Vesical Neck for Urinary Incontinence in Females*, Ann. Surgery, pp. 465–471, October 1980; and Pereyra, *A Simplified Surgical Procedure for the Correction of Stress Incontinence in Women*, West. J. Surg., Obstetrics & Gynecology, pp. 243–246, July–August 1959.

A pubovaginal sling procedure is a surgical method involving the placement of a sling to stabilize or support the bladder neck or urethra. There are a variety of different sling procedures. Descriptions of different sling procedures and surgical articles used therein are disclosed in U.S. Pat. Nos. 5,112,344; 5,611,515; 5,842,478; 5,860,425; 5,899,909; 6,039,686; 6,042,534 and 6,110,101.

Some prior art needles include a metal needle and an integral metal handle. Some users consider such needles to be top heavy or imbalanced. During some surgical procedures, the needles may be partially inserted in the body and released, as the surgeon concentrates on a different aspect of the surgery. In such instances a top heavy needle may deflect or deviate from its intended placement, potentially damaging tissue or causing other undesirable consequences.

SUMMARY OF THE INVENTION

The present invention is directed to a surgical instrument. The surgical instrument is particularly suitable for addressing pelvic disorders.

The surgical instrument includes a handle, and an elongate, preferably curved rod with a distal tip. The length of the rod is preferably between about 6 inches and about 12 inches. The height of the handle is preferably between about 3.25 inches and about 4.75 inches. Preferably, the rod comprises stainless steel and at least one material comprising the handle is a polymer with a density less than the stainless steel density.

The handle has a major anterior surface, preferably situated to face a surgeon with the rod extending generally toward the surgeon, a major posterior surface and minor side surfaces.

Preferably, the handle has a height more than forty percent of the length of the rod and less than eighty percent of the length of the rod, and the depth of the handle is less than the height of the handle.

In curved embodiments, the rod has a radius that is between 4.5 and 5.5 inches. Preferably, the distal tip is substantially blunt.

The major anterior surface of the handle preferably includes an elongate channel extending across the width of the handle. Preferably, the anterior surface of the handle has at least four tactile surfaces. In embodiments that include the channel, the tactile surfaces are preferably located distal to the elongate channel.

The major posterior surface of the handle preferably includes an elongate depression having an axis that extends substantially parallel to the longitudinal axis of the handle. The anterior surface also preferably has a plurality of tactile surfaces extending in a direction substantially perpendicular to the longitudinal axis of the handle.

The handle preferably includes a flare at a proximal end portion. In embodiments with the flare, the major posterior surface includes a substantially concave surface and the major anterior surface includes a substantially convex surface.

In a preferred embodiment, at least two thirds of the exterior surface of the elongate rod includes a surface treatment. This can comprise a sandblasted surface.

In another aspect, the present invention comprises the ornamental design for a handle for a surgical instrument, as shown in FIGS. 8 through 14 and described in the Brief Description of the Drawings.

The handle may be molded with a single polymeric material. Alternatively, the handle may comprise a plurality of different polymeric materials. Also optionally, the handle may comprise a metal or metal components (e.g. an insert, or a straight portion of the rod).

BRIEF DESCRIPTION OF THE DRAWINGS

Other features and advantages of the present invention will be seen as the following description of particular embodiments progresses in conjunction with the drawings, in which:

FIG. 9 is a right side view of the design of a handle for a surgical instrument of FIG. 8;

FIG. 10 is a left side view of the design of a handle for a surgical instrument of FIG. 8;

FIG. 15 is a side view of another embodiment of a surgical instrument according to the present invention;

FIG. 16 is a sectional view taken approximately along lines 16—16 of FIG. 15;

FIG. 17 is another cross section for another embodiment of surgical instrument according to the present invention;

FIG. 18 is another cross section for another embodiment of surgical instrument according to the present invention;

FIG. 19 is another cross section for another embodiment of surgical instrument according to the present invention; and FIG. 20 is another cross section for another embodiment of surgical instrument according to the present invention.

Figure 1:
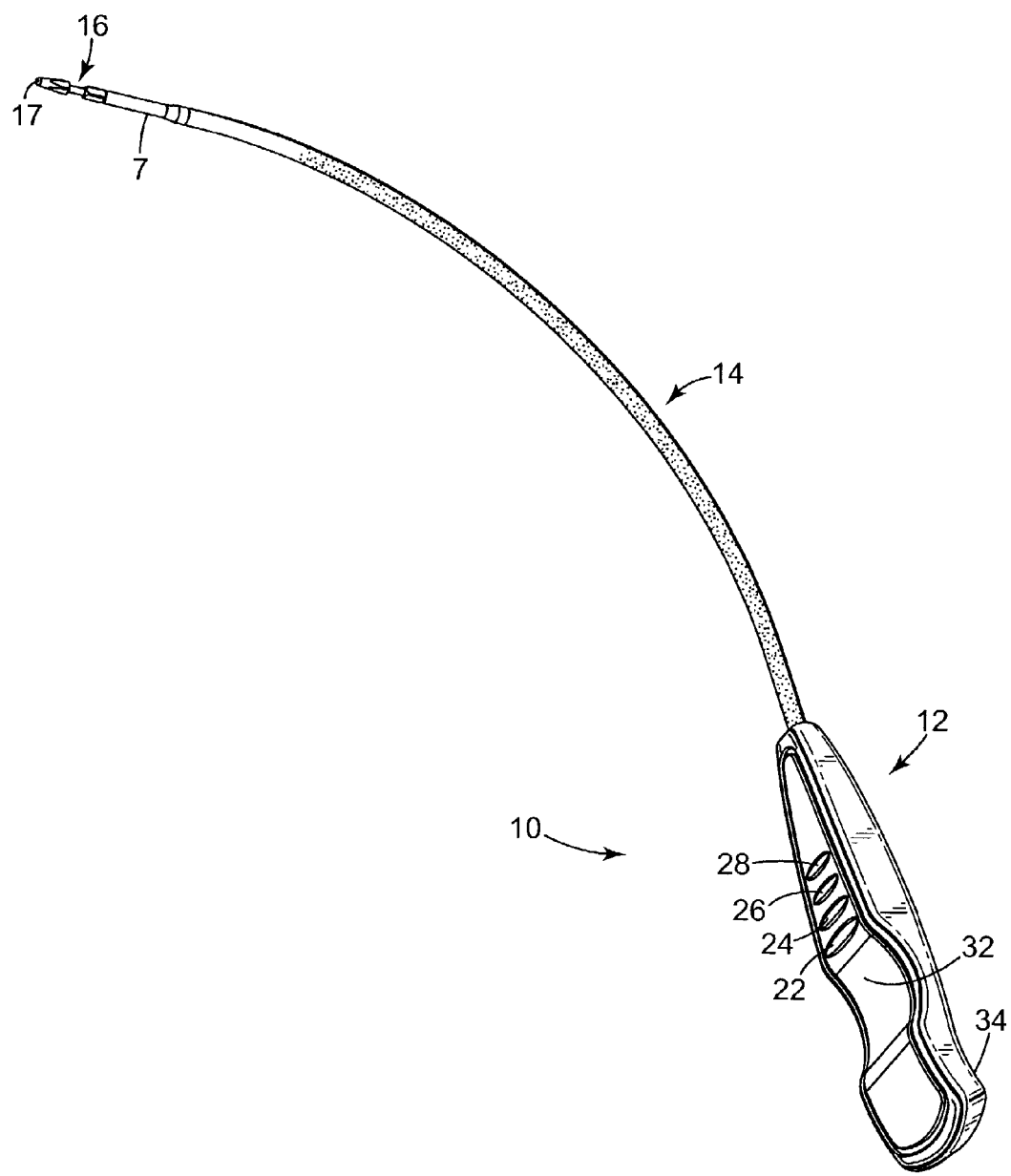
FIG. 1 is a perspective view of the surgical instrument according to the present invention.

The broken line showing of a needle and surface structures on the design of the handle in FIGS. 8 through 14 are for illustrative purposes only and form no part of the claimed design.

DETAILED DESCRIPTION

The following description is meant to be illustrative only and not limiting. Other embodiments of this invention will be apparent to those of ordinary skill in the art in view of this description.

The present invention is directed to surgical instruments for treating pelvic floor disorders such as incontinence or stress urinary incontinence (SUI) in both men and women. Although the invention as disclosed herein generally refers to SUI, the surgical instruments may be used for treatment of other urological or gynecological disorders, such as prolapse (e.g. vaginal and uterine), enteroceles (e.g. of the uterus or small bowel), rectoceles, cystoceles and other disorders are also included within the scope of the present invention. The present invention is particularly suitable for use in conjunction with concomitant procedures, such as, but not limited to, procedures for addressing cystocele, rectocele, vaginal prolapse and anatomic corrections.

Referring now to FIGS. 1–7, there is shown a preferred embodiment of surgical instrument 10 according to the present invention. The surgical instrument 10 comprises a handle 12 having a width W, height H and depth D, and an elongate, slender, metal, curved rod 14. The rod 14 emerges from the handle 12, and has a proximal end portion permanently fixed within the handle 12. By slender, it is meant for example, for the embodiments of the present invention with a circular cross sectional shape (e.g. see FIG. 16), the major portion of the rod 14 along its length has a diameter less than about 4 mm, more preferably about 3.2 mm. The handle 12 is preferably rigidly or permanently affixed to the rod 14.

The rod 14 preferably has a curved axis, and a distal end portion 16. The distal end portion 16 preferably has a substantially blunt distal tip 17. As used herein, when it is said that the rod 14 is curved or has a curved axis, it is understood that the entire rod 14 need not be curved. Indeed, the rod preferably has at least some straight portions (e.g. preferably the portion within the handle 12, and optionally portions of the distal end portion 16). Thus, it is expressly understood that a curved rod can have segments or portions that are substantially straight, and that the rod need not be uniformly curved along the same radius.

in FIGS. 1–7, the distal end portion 16 of the instrument 10 includes a reduced diameter portion 7 and a frustoconical portion between the reduced diameter portion 7 and the rest of the rod 14. The distal end portion 16 optionally has structure for associating the instrument 10 with another surgical article (e.g. a connector, dilator, sling assembly, sling or suture). Optionally, the distal end portion 16 may incorporate specially designed surfaces for cooperating with complementary surfaces on another surgical article, such as the structures described in U.S. Pat. Application Publication No. 2002/0099259, published Jul. 25, 2002 (U.S. patent application Ser. No. 09/917,445, filed Jul. 27, 2001), or U.S. Pat. Application Publication No. 2002/0151762, published Oct. 17, 2002 or U.S. Pat. Application Publication No. 2002/0147382 published Oct. 10, 2002.

Figure 15A:
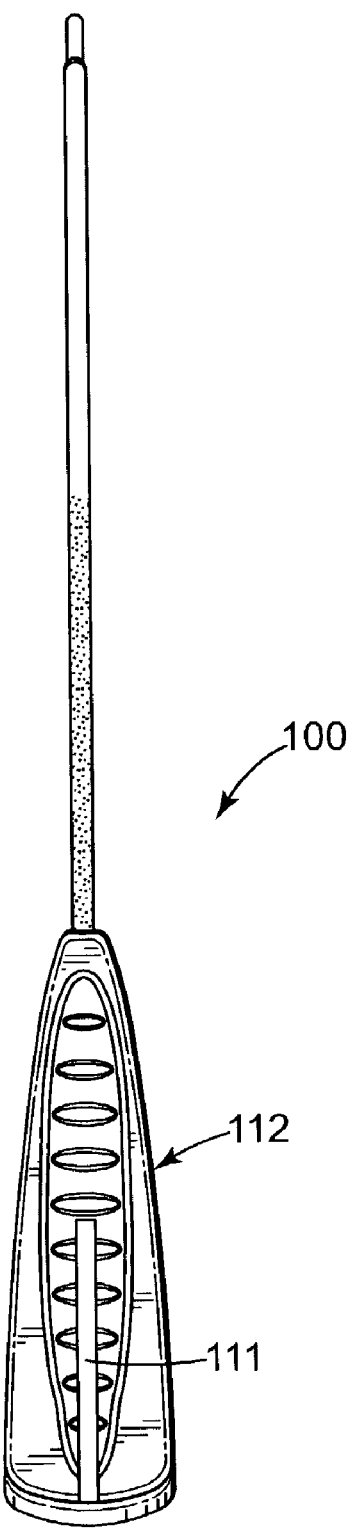
FIG. 15A is a rear view of the instrument of FIG. 15.

FIGS. 15 and 15A show an alternative embodiment of surgical instrument 100 in accordance with the present invention. In this embodiment, the instrument 100 includes an eyelet E in its distal portion with a distal tip 107. Alternatively, other structures such as a hook, clip, catch, J-shaped groove, channel, slot, hasp, latch, key, bodkin, carbineer-like connector or other structure is within the scope of the present invention.

Figures 2, 3:
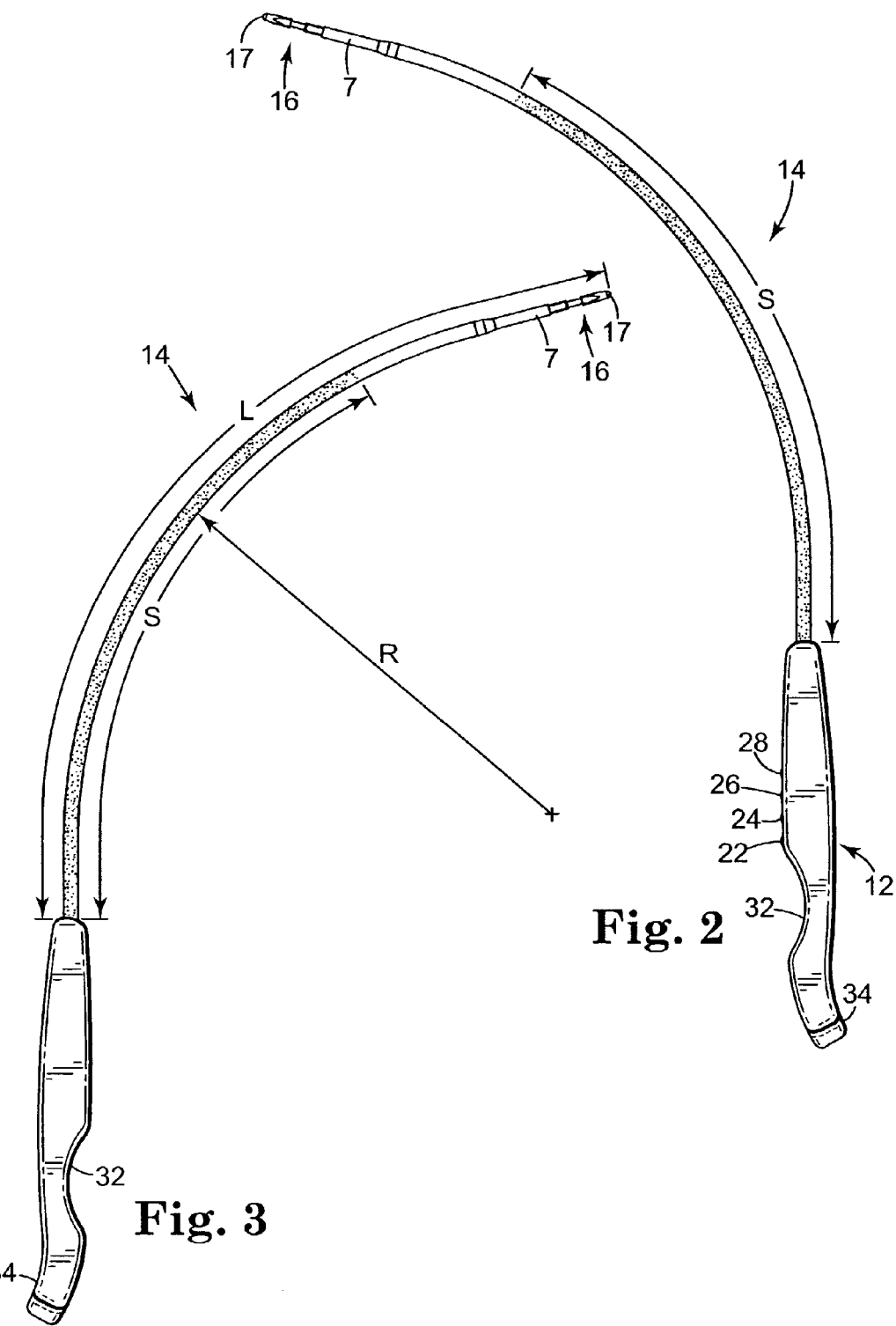
FIG. 2 is a right side view of the surgical instrument of FIG. 1, showing a side surface of the handle.
FIG. 3 is a left side view of the surgical instrument of FIG. 1, showing a side surface of the handle.

Referring to FIG. 3, the rod 14 of the instrument 10 preferably has at least a portion with a radius R and a length L along the curved axis between distal tip 17 of the rod 14 and a point on the rod axis where the rod emerges from the handle (see FIG. 3). The length L is preferably between about 6 inches and about 12 inches, more preferably between about eight inches and about nine inches, even more preferably about 8.25 inches. The radius R is preferably between 4.5 and 5.5 inches. Notably, the entire portion of the rod 14 need not be continuously curved or situated along the same radius R. Preferably, the portion of the rod 14 within the handle 12 and the distal portion 16 are not curved along the same radius R, and instead, these portions are preferably substantially straight.

Figure 4:
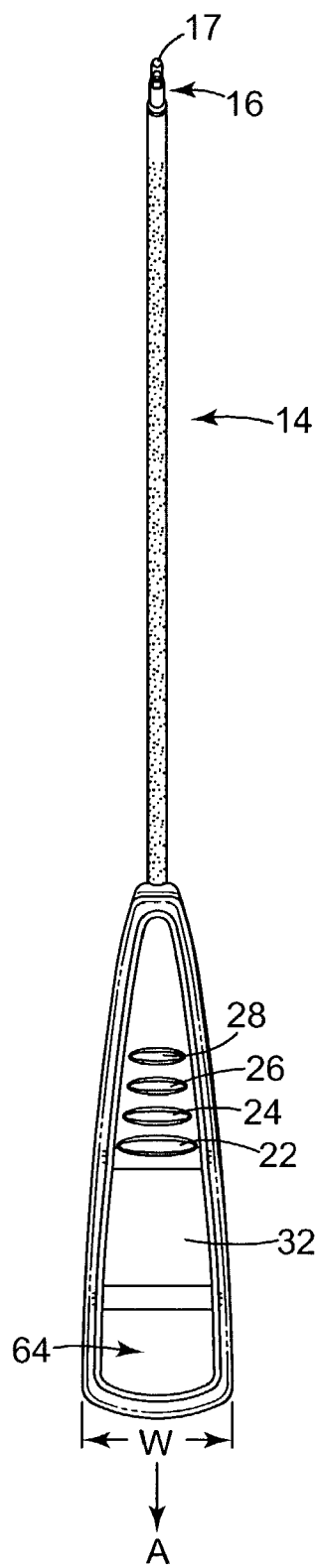
FIG. 4 is a top view of the surgical instrument of FIG. 1, showing a major anterior surface of the handle.

The handle 12 has a major anterior surface 64 that is best seen in FIG. 4. The major anterior surface 64 has width W and height H. The height H of the handle 12 is preferably between about 3.25 inches and about 4.75 inches. Referring to FIG. 1, the major anterior surface is situated to face a surgeon with the rod 14 extending toward the surgeon.

Figure 5:
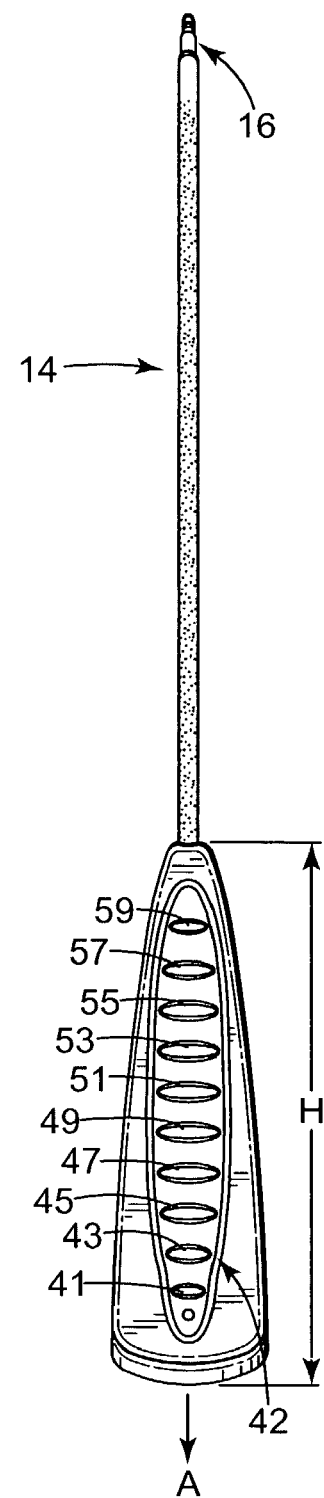
FIG. 5 is a bottom view of the surgical instrument of FIG. 1, showing a major posterior surface of the handle.

The handle 12 also has a major posterior surface 42 that is best seen in FIG. 5 that also has a width W and height H. Notably, the width W of the handle 12 is in a direction that is substantially perpendicular to the axis of the rod 14 (see FIG. 4). The major posterior surface 42 of the handle preferably includes an elongate depression having an axis that extends substantially parallel to the longitudinal axis of the handle (see the substantially oval shape in FIG. 5). The depression is preferably substantially concave, but could alternatively be convex.

Figure 6:
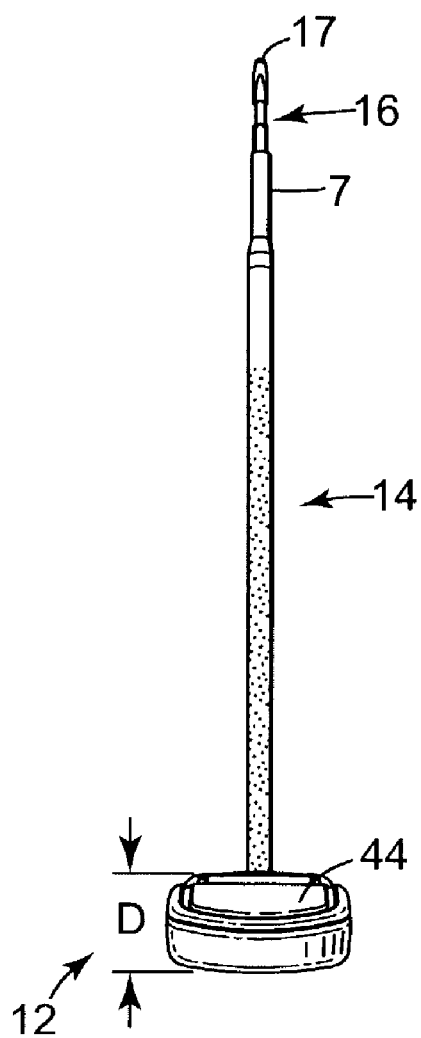
FIG. 6 is a front end view of the surgical instrument of FIG. 1.
Figure 7:
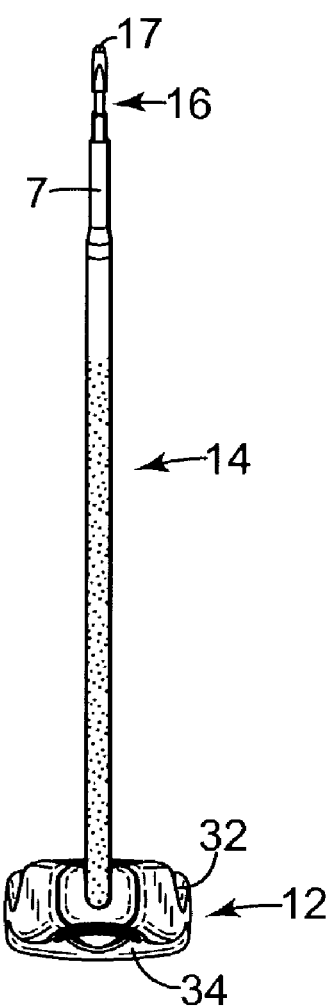
FIG. 7 is a rear end view of the surgical instrument of FIG. 1.
Figure 8:
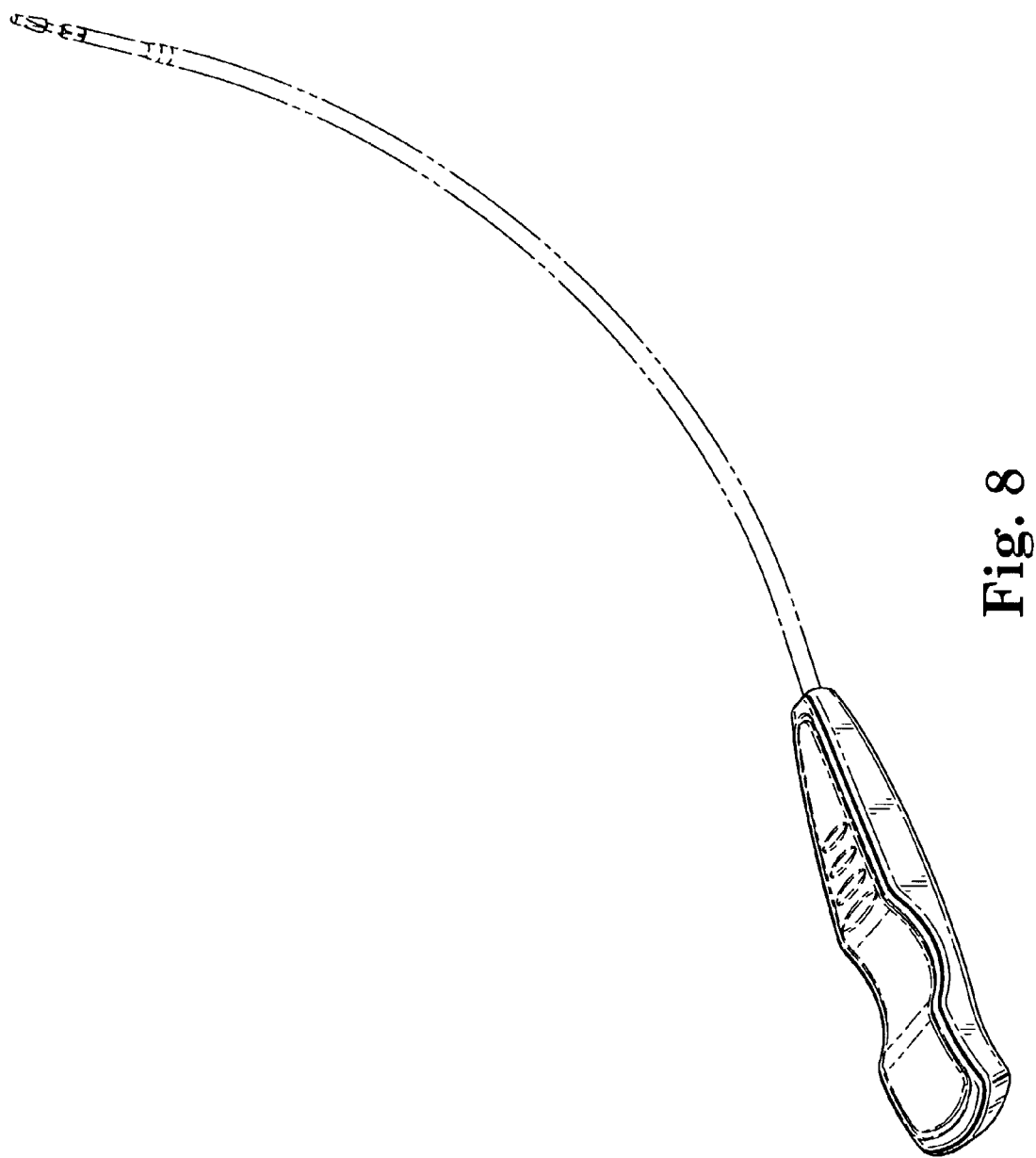
FIG. 8 is a perspective view of a design of a handle for a surgical instrument according to another aspect of the present invention.
Figure 11:
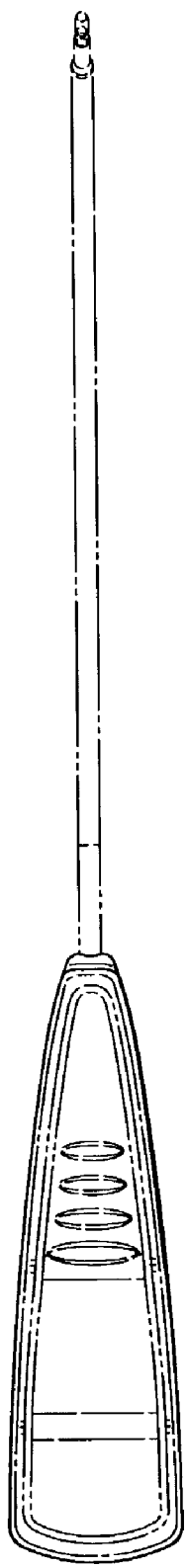
FIG. 11 is a top view of the design of a handle for a surgical instrument of FIG. 8.
Figure 12:
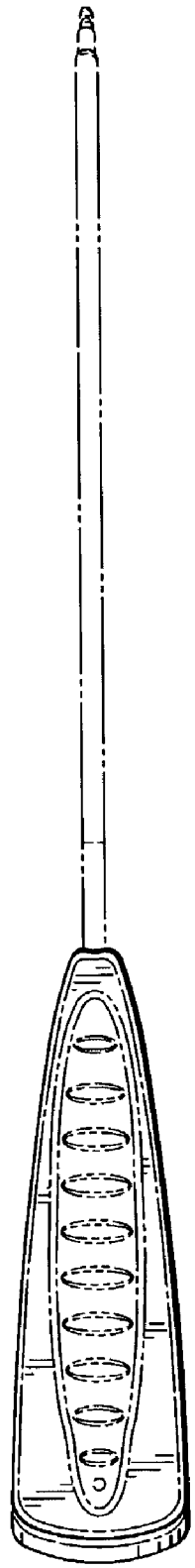
FIG. 12 is a bottom view of the design of a handle for a surgical instrument of FIG. 8.
Figure 13:
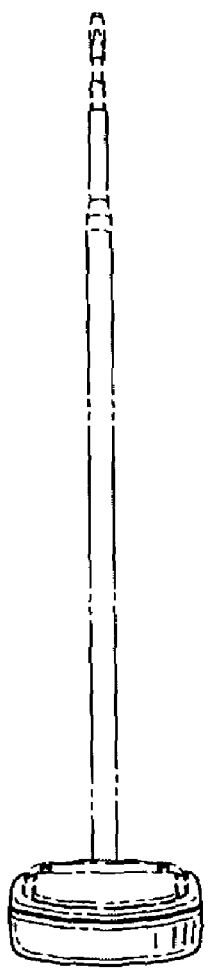
FIG. 13 is a front end view of the design of a handle for a surgical instrument of FIG. 8.
Figure 14:
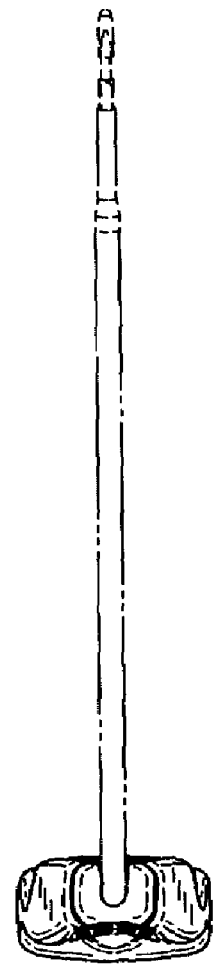
FIG. 14 is a rear end view of the design of a handle for a surgical instrument of FIG. 8.

Referring to FIGS. 2, 3 and 6, the handle 12 also has minor side surfaces having a depth D and height H. The depth D of the handle 12 is less than the height H of the handle 12.

The handle 12 preferably has a height H that is more than forty percent of the length L of the rod 14 and less than eighty percent of the length L of the rod 14.

The rod 14 may be rigid or malleable. Preferably, the rod 14 is a hardened steel component. A variety of different materials may be used to construct the surgical instrument including, but not limited to medical grade plastics and metals. Suitable materials include titanium, stainless steel, other medical grade alloys. Suitable stainless steels include AISI types 316, 316l, 17–4, 302, 303 and 304.

The handle 12 has a longitudinal axis A along its height H. The handle 12 preferably includes an elongate channel 32 extending across the width W of the handle 12. The channel 32 has an axis that extends substantially perpendicular to the longitudinal axis A of the handle 12. The height (length) of the channel 32 along the longitudinal axis A of the handle 12 is more than 0.5 inches and less than 1 inch, more preferably the length is about 0.9 inches. The depth of the channel 32 is preferably between 25% and 100% of the depth of the handle 12.

The rod 14 preferably comprises stainless steel and at least one material comprising the polymeric handle 12 has a density less than stainless steel.

The height H to width W ratio of the handle 12 is preferably greater than 3:1, and the depth D to width W ratio is preferably less than 1:2.

Referring to FIGS. 1 and 4, the anterior surface 64 preferably has a plurality of tactile surfaces 22, 24, 26 and 28 extending in a direction substantially perpendicular to the longitudinal axis A of the handle 12. Preferably, there are at least four tactile surfaces 22, 24, 26 and 28. The handle 12 has proximal and distal ends and the rod 14 emerges from the distal end of the handle. The tactile surfaces 22, 24, 26 and 28 are preferably located distal to the elongate channel 32. In a preferred embodiment, they are located on the bottom (distal) two thirds of the handle 12. The tactile surfaces may extend above the major anterior surface 64, or below the major anterior surface. They may comprise slits, slots, bumps, protrusions, ridges, ribs, grooves or the like.

The handle 12 preferably includes a flare 34 at a proximal end portion. In this embodiment, the posterior surface 42 preferably includes a substantially concave surface and the anterior surface 64 includes a substantially convex surface adjacent the proximal end portion of the handle 12.

The surgical instrument 10 may have a portion of the exterior surface of the rod 14 polished and a portion treated. In the embodiment shown in FIG. 3, at least two thirds of the exposed, exterior surface of the elongate rod 14 preferably includes a surface treatment for enhancing grasping of the rod 14. Suitable treatments include but are not limited to peening, sand blasting, knurling, engraving, chemical and laser etching, heat etching, carving, scoring and other techniques. This may be accomplished by masking a portion or portions of a polished rod and bombarding unmasked portions of the rod with silica emerging through a pressurized nozzle (sand blasting).

Preferably, at least the portion of the exposed rod 14 nearest the handle 12 is treated to increase its coefficient of friction and the portion or portions of the rod 14 remote from the handle 12 are polished. The portion of the rod 14 treated may include a predetermined pattern or selected areas or zones. The portion of the exposed rod 14 that is treated is preferably between about 5% and 98% of the length of the exposed rod 14, more preferably, it is between about 50% and 95%. In the embodiment depicted in FIG. 3, it is about 66%.

Rather than grasping the handle 12, which may isolate tactile sensation, the surface treatment allows grasping of a surface which allows for better tactile sensation for the physician passing the rod 14 through anatomical structures. Portions or patterns may be treated on the rod 14 to provide the necessary handling or visual characteristics. Specifically, when using cystoscopy to look for surgical trauma caused by the rod 14 to the bladder, by having only a portion of the rod 14 treated creates an altered light diffraction pattern so the otherwise reflective surface of the rod 14 may be more easily seen when immersed in liquid filling the bladder. The pattern of treatment may also identify the instrument by size, length, depth of penetration or other feature useful for facilitating surgical use of the instrument.

The surface texturing is preferably sufficiently deep to enhance handling of the surgical instrument, but does not significantly alter the mechanical strength of the material.

The surface texturing preferably extends a predetermined distance along the rod. In one embodiment, the leading (distal) end 16 of the rod 14 is free of surface texturing and has a substantially smooth surface. The trailing end of the rod (the portion emerging from handle 12) has surface texturing extending a sufficient length to enhance handling of the instrument 10. The surface texturing does not extend unduly, such as to an extent where the texturing may unduly abrade or damage sensitive tissue during anticipated uses.

Referring to FIG. 5, the posterior surface 42 has a plurality of tactile surfaces (e.g. protrusions or slots) 41, 43, 45, 47, 49, 51, 53, 55, 57 and 59 extending in a direction substantially perpendicular to the longitudinal axis A of the handle 12. Preferably, the posterior surface has at least five tactile surfaces, and more preferably at least ten tactile surfaces.

The materials of the handle 12 can comprise any suitable material for a surgical instrument. They are preferably polymeric materials such as, but not limited to polycarbonate, polyethylene, polypropylene, polyvinyl chloride (PVC), polytetrafluoroethylene (PTFE), delrin, ABS, polyurethane, nylon, acetal, urethane, polyetherimide, polysulfone or other similar sterilizable materials, including combinations thereof.

The major anterior and posterior surfaces 42 and 64 may be constructed in a plurality of different fashions. Molding, casting and machining processes may be utilized. The surfaces 42 and 64 may comprise a monolithic, unitary or composite injection molded components.

The surgical instrument 10 may be constructed using a two-part molding process. The rod 14 is placed in a first base handle mold. A first polymer is injected molded to form a portion of the handle 12 (e.g. including the periphery of the minor side portions). One or more slots on the portion of the rod 14 designed to be within the handle 12 can help facilitate proper molding between the materials of the handle 12 and the rod 14.

The first base handle mold can form, for example, the portion of the handle 12 that does not include the tactile surfaces 22, 24, 26, 28, 41, 43, 45, 47, 49, 53, 55, 57 and 59. The first polymeric material can comprise any suitable polymer such as a copolymer of acrylonitrile, butadiene and styrene (ABS). One suitable material is Bayer's Lustran ABS.

An insert or other portion of the first mold is used to preserve room for a second injection molding (an overmold) of a second polymeric material. For example, the second injection molding may form the tactile surfaces 22, 24, 26, 28, 41, 43, 45, 47, 49, 53, 55, 57 and 59 on both the major anterior and major posterior surfaces. Any suitable polymeric material may be used for the overmolding process. Suitable examples include, but are not limited to Pellethane urethane, or Santoprene S-79956 from Advanced Elastomer Systems. The second material may run through the handle 12, connecting the major anterior and posterior surfaces.

Referring now to FIGS. 15 and 15A, the surgical instrument 100 includes an indicator arm 111 which may be sized, shaped and situated to provide information on the path of the distal end of the rod 114. Optionally, the indicator arm 111 may be deployable (movable) relative to the rest of the handle. Also optionally, as shown with the dashed lines in FIG. 15, the handle 112 may include a groove for receiving the arm 111. In this embodiment, the surface texturing S' runs about 50% of the length of the rod 114.

now to FIGS. 16–20, the cross sectional shape of the rod 114 (and rod 14) may comprise any suitable polygonal shape including circular (FIG. 16), oval (FIG. 17), elliptical or egg-shaped (FIG. 18), rectangular (FIG. 19), triangular (FIG. 20) or combinations thereof.

FIGS. 8 through 14 show an ornamental design for a handle for a surgical instrument according to another aspect of the present invention. The broken line showing in these Figures of a needle and surface structures on the design of the handle are for illustrative purposes only and form no part of the claimed design.

Notably, the surgical instruments 10 and 100 are only embodiments of the present invention, and one of ordinary skill in the art who is exposed to this disclosure will recognize that other embodiments and representations are within the scope of the present invention. For example, the handles 12 and 112 are substantially wedge-shaped. Embodiments of the surgical instrument of the present invention include substantially rectangular shaped handles. In other aspects, the surgical instruments of the present invention can comprise those shown and described in U.S. Provisional Application Ser. No. 60/343,658, filed Oct. 24, 2001; and U.S. Provisional Application Ser. No. 60/336,884, filed Nov. 2, 2001; and U.S. Provisional Application Ser. No. 60/347,494, filed Jan. 11, 2002.

The surgical instruments according to the present invention may be reusable, single use, or disposable.

All patents, patent applications, and publications cited herein are hereby incorporated by reference in their entirety as if individually incorporated.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical instrument for addressing pelvic disorders comprising:
   a handle having a width, height and depth and a longitudinal axis along the handle height; and
   an elongate, slender, metal, curved rod emerging from the handle, the rod having a proximal end portion permanently fixed to the handle, a curved axis, and a distal end portion having a distal tip, the elongate curved rod having at least a portion with a radius and a length along the curved axis between the distal tip of the rod and a point on the rod axis where the rod emerges from the handle; and
   wherein:
   the handle has a major anterior surface having a width and height, the major anterior surface being situated in use to face a surgeon with the rod extending generally toward the surgeon, a major posterior surface having a width and height that includes an elongate, substantially oval-shaped depression having an axis that extends substantially parallel to the longitudinal axis of the handle, at least two minor side surfaces having a depth and height, the width of the handle being in a direction that is substantially perpendicular to the axis of the rod,
   the height of the handle is more than about forty percent of the length of the rod and less than about eighty percent of the length of the rod, and
   the depth of the handle is less than the height of the handle.

2. A surgical instrument according to claim 1 wherein the rod has a length between about 6 inches and about 12 inches and is curved along a substantial portion of its axis with a radius of curvature that is between 4.5 and 5.5 inches, and the distal tip is substantially blunt.

3. A surgical instrument according to claim 1 wherein the major anterior surface of the handle includes an elongate channel extending across the width of the handle, the channel having an axis that extends substantially perpendicular to the longitudinal axis of the handle, and the length of the channel along the longitudinal axis of the handle being more than 0.5 inches and less than 1 inch.

4. A surgical instrument according to claim 1 wherein the rod comprises stainless steel and at least one material comprising the handle is a polymer with a density less than the stainless steel density.

5. A surgical instrument according to claim 1 wherein the handle height to width ratio is greater than 3:1.

6. A surgical instrument according to claim 1 wherein the anterior surface has a plurality of tactile surfaces extending in a direction substantially perpendicular to the longitudinal axis of the handle.

7. A surgical instrument according to claim 6 wherein the handle has a proximal and distal end, with the rod emerging from the distal end of the handle, and the handle includes an elongate channel with an axis that extends substantially perpendicular to the longitudinal axis of the handle, and the tactile surfaces are located distal to the elongate channel.

8. A surgical instrument according to claim 6 wherein the posterior surface has a plurality of tactile surfaces extending in a direction substantially perpendicular to the longitudinal axis of the handle.

9. A surgical instrument according to claim 6 wherein the anterior surface includes at least four tactile surfaces.

10. A surgical instrument according to claim 9 wherein the tactile surfaces comprise grooves.

11. A surgical instrument according to claim 1 wherein the handle includes polycarbonate.

12. A surgical instrument according to claim 1 wherein the major posterior surface has a plurality of tactile surfaces with axes substantially perpendicular to the longitudinal axis of the handle.

13. A surgical instrument according to claim 12 wherein the tactile surfaces comprise protrusions.

14. A surgical instrument according to claim 1 wherein the handle includes a flare at a proximal end portion, the major posterior surface includes a concave surface, and the major anterior surface includes a convex surface.

15. A surgical instrument according to claim 1 wherein at least two thirds of the exterior surfaces of the elongate rod includes a surface treatment for enhancing grasping of the rod.

16. A surgical instrument according to claim 1 wherein depth to width ratio of the handle is less than 1:2.

17. A surgical instrument for addressing pelvic disorders comprising:
   a handle having a width, height and depth; and
   an elongate, slender, metal, rod emerging from the handle, the rod having a proximal end portion permanently fixed to the handle, an axis, and a distal end portion having a substantially blunt distal tip, the elongate rod having a length along the axis between the distal tip of the rod and a point on the rod axis where the rod emerges from the handle; and wherein:

the handle has a major anterior surface having a width and height, a major posterior surface having a width and height, and minor side surfaces extending between the major anterior and posterior surfaces and each having a depth and height, the width of the handle is in a direction that is substantially perpendicular to the axis of the rod, the height of the handle is more than about forty percent of the length of the rod and less than about eighty percent of the length of the rod, the depth of the handle is less than the height of the handle, the handle has a longitudinal axis along its height, the major anterior surface of the handle has an elongate channel extending across the width of the handle, the channel having an axis that extends substantially perpendicular to the longitudinal axis of the handle, the handle has a proximal and distal end, with the rod emerging from the distal end of the handle, a flare is at a proximal end portion of the handle, and the major posterior surface has a substantially concave surface and the anterior surface has a substantially convex surface.

18. A surgical instrument according to claim 17 wherein the major posterior surface of the handle includes an elongate depression having an axis that extends substantially parallel to the longitudinal axis of the handle.

19. A surgical instrument for addressing pelvic disorders comprising:

a handle having a width, a depth, a height extending between handle proximal and distal ends, and a longitudinal axis along the handle height; and an elongate, slender, metal, curved rod coupled to the handle, the rod having a proximal end portion permanently fixed to the handle to extend distally from the handle distal end, a curved axis, and a distal end portion having a distal tip, the elongate curved rod having at least a portion with a radius and a length along the curved axis between the distal tip of the rod and a point on the rod axis where the rod is fixed to the handle; and wherein:

the width of the handle is in a direction that is substantially perpendicular to the axis of the rod, the height of the handle is more than about forty percent of the length of the rod and less than about eighty percent of the length of the rod, the depth of the handle is less than the height of the handle, the handle has a major posterior surface having a width and height, a major anterior surface having a width and height, and at least two minor side surfaces having a depth and height extending between the major anterior and posterior surfaces, the anterior surface being situated in use to face a surgeon with the rod extending generally toward the surgeon, and the anterior surface has an elongate channel with an axis that extends substantially perpendicular to the longitudinal axis of the handle and a plurality of tactile surfaces extending in a direction substantially perpendicular to the longitudinal axis of the handle and located on the anterior surface between the elongate channel and the handle distal end.

* * * * *